(12) United States Patent
Sonoda et al.

(10) Patent No.: US 7,611,492 B2
(45) Date of Patent: Nov. 3, 2009

(54) PUNCTURE DEVICE

(75) Inventors: Yutaro Sonoda, Ashigarakami-gun (JP); Tetsuro Kawanishi, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 210 days.

(21) Appl. No.: 11/594,925

(22) Filed: Nov. 9, 2006

(65) Prior Publication Data

US 2007/0167970 A1 Jul. 19, 2007

Related U.S. Application Data

(60) Provisional application No. 60/735,200, filed on Nov. 10, 2005.

(51) Int. Cl.
*A61M 5/178* (2006.01)
*A61M 5/32* (2006.01)

(52) U.S. Cl. .................. 604/164.04; 604/175; 604/159

(58) Field of Classification Search ................. 604/174, 604/175, 180, 272–274, 158–161, 164.01, 604/164.04, 164.07, 164.09, 239, 159, 171; 606/185, 213; 128/DIG. 26
See application file for complete search history.

(56) References Cited

U.S. PATENT DOCUMENTS

| | | | |
|---|---|---|---|
| 4,345,601 A | * | 8/1982 | Fukuda ..................... 606/147 |
| 5,390,671 A | | 2/1995 | Lord et al. |
| 5,437,640 A | | 8/1995 | Schwab |
| 5,605,152 A | | 2/1997 | Slate et al. |
| 6,413,245 B1 | | 7/2002 | Yaacobi et al. |
| 6,494,865 B1 | | 12/2002 | Alchas |
| 6,592,552 B1 | | 7/2003 | Schmidt |
| 6,994,691 B2 | | 2/2006 | Ejlersen |
| 2005/0256499 A1 | | 11/2005 | Pettis et al. |
| 2007/0156096 A1 | | 7/2007 | Sonoda et al. |

FOREIGN PATENT DOCUMENTS

| | | |
|---|---|---|
| JP | 57-139358 A | 8/1982 |
| JP | 7-275227 A | 10/1995 |
| JP | 8-107890 A | 4/1996 |
| JP | 2001-137343 A | 5/2001 |
| JP | 2001-516625 A | 10/2001 |
| JP | 2003-511204 A | 3/2003 |
| JP | 2005-087519 A | 4/2005 |
| JP | 2005-518253 A | 6/2005 |

OTHER PUBLICATIONS

Sonoda, et al., U.S. Appl. No. 11/594,825, entitled, "Puncture Device," filed Nov. 9, 2006.

* cited by examiner

*Primary Examiner*—Kevin C. Sirmons
*Assistant Examiner*—Catherine N Witczak
(74) *Attorney, Agent, or Firm*—Buchanan Ingersoll & Rooney PC

(57) ABSTRACT

A puncture device which can stick a puncture needle certainly to a predetermined region of a skin includes a puncture needle having a curvature portion, a retaining member retaining the puncture needle, an indwelling device adapted to be indwelled in a living body by way of the puncture needle, and a guide member mounted at a predetermined position of a body surface. The puncture needle is adapted to be stuck into the skin along the guide member.

13 Claims, 9 Drawing Sheets

PUNCTURE DEVICE

TECHNICAL FIELD

The present invention relates to a puncture device and more specifically relates to a puncture device which punctures from a skin surface and is used with respect to a predetermined region, for example, a dermis.

BACKGROUND ART

It is known that the dermis has a high density of capillary blood vessels when compared with an epidermis or a subcutis and also a lymph vessel end exists therein, so that in particular, a medical agent injected thereto directly is shifted to a blood vessel or a lymph vessel and an absorption speed thereof being absorbed in the body fluid is speedy. In particular, it is possible in the dermis to make a medical agent using a macromolecular substance such as hormone, antibody drug, cytokine and the like to be absorbed into the blood efficiently. Also, it is known that the dermis is a place of efficient immunity and it is possible to make a saving of applied dose of vaccine or to strengthen sensitization of a weak vaccine.

Also, it is known for adult human beings that the dermis exists approximately at a certain depth from the body surface (surface of stratum corneum). In other words, this fact means in case of injecting a medical agent into the dermis that it is possible to use a puncture needle having the same length (depth) with respect to these human beings.

Generally, the width of the dermis D is around 1 mm to 4 mm (average value is 1 mm to 2 mm) if the vertical direction with respect to the body surface F is made to be a reference and also, as shown in FIG. 10, the dermis D exists in the skin so as to be sandwiched between an epidermis E which includes a stratum corneum SC and has width of around 0.06 mm to 0.1 mm and a subcutis S.

Accordingly, it is difficult to insert a tip portion of the puncture device, for example, a needlepoint of the puncture needle accurately to the dermis which exists between the epidermis and the subcutis and if the needlepoint is inserted erroneously to the subcutis or the like, there occurs a problem such that a medical agent cannot be absorbed efficiently.

In recent years, for example, it is attempted that the macromolecular medicine mentioned above is administered continually or by one-shot into the dermis as a target and in such a case, in particular, the above-mentioned problem becomes conspicuous.

Here, a hypodermic injection device is known in which the length of the puncture needle to be inserted into a living body is defined in order to inject a medical agent to the dermis in the body (JP2007-137343). In addition, a medicinal solution injection device is also known in which the depth (insertion depth) of the puncture needle to be inserted into the skin is defined to be a predetermined length in order to inject a medical agent into a specific layer which exists in the skin and the puncture needle is inserted into the skin from the vertical direction with respect to the body surface (JP2005-087519).

DISCLOSURE OF THE INVENTION

Problem to be Solved by the Invention

However, there is employed in these devices a constitution in which the puncture needle is inserted into the skin from the vertical direction with respect to the body surface. In this case, if it is attempted to puncture with the puncture needle, the whole skin is sunk in elastically so as not to be punctured and also, even if it is punctured, it sometimes happens that the needlepoint cannot reach the dermis.

Also, when the puncture needle is inserted perpendicularly with respect to the dermis, the depth (insertion depth) of the puncture needle in the dermis becomes short and, for example, in such a case where some kind of impact or the like is added from the outside, there occurs a problem in which the puncture needle during injecting a medical agent drops out from the dermis.

Further, in case of using these devices, the distance from an insertion aperture of the puncture needle which is formed on the surface of the dermis (boundary portion of epidermis and dermis) until a medical agent releasing opening which exists at the tip of the puncture needle becomes short in the dermis in which there happens a problem that the medical agent injected to the dermis from the medical agent releasing opening is to leak from the insertion aperture to the outside of the dermis (epidermis).

In consideration of the above-mentioned problems, an object of the present invention lies in providing a puncture device which can stick a puncture needle certainly to a predetermined region of a skin.

Means for Solving the Problem

Such an object is accomplished according to the present invention of the following (1) to (10).

(1) In a puncture device puncturing a skin by a puncture needle, a puncture device characterized by including:

a device main body having a contact surface which contacts said skin;

a puncture needle having a curvature portion of a predetermined curvature radius; and a puncture needle moving means provided in said device main body for moving said puncture needle along a circular trajectory which said curvature radius draws so as to puncture said skin.

(2) In a puncture device puncturing a skin by a puncture needle, a puncture device comprising:

a puncture needle having a curvature portion;

a retaining member retaining the puncture needle;

an indwelling device indwelled in a living body by said puncture needle; and a guide member mounted at a predetermined position of a body surface, characterized by being constituted such that said puncture needle is to be stuck to said skin along said guide member.

(3) The puncture device according to aforesaid (2), characterized in that a curved surface of such a shape along the curvature of said puncture needle is formed on said guide member.

(4) The puncture device according to aforesaid (3), characterized in that there is formed on said retaining member a curved surface of such a shape along a curved surface which is formed on said guide member.

(5) In a puncture device puncturing a skin by a puncture needle, a puncture device comprising:

a hollow puncture needle having a curvature portion;

a retaining member retaining this puncture needle;

an indwelling device indwelled in a living body by said puncture needle;

a fixing member for fixing said indwelling device; and a guide member mounted at a predetermined position of the body surface, characterized by being constituted such that said puncture needle punctures said skin along said guide member.

(6) The puncture device according to aforesaid (5), characterized in that a curved surface of such a shape along the curvature of said puncture needle is formed on said guide member.

(7) The puncture device according to aforesaid (6), characterized in that there is formed on said retaining member a curved surface of such a shape along a curved surface which is formed on said guide member.

(8) In a puncture device puncturing a skin by a puncture needle, a puncture device comprising:
a puncture needle having a curvature portion;
a retaining member retaining this puncture needle; and
a guide member mounted at a predetermined position of a body surface, characterized by being constituted such that
said puncture needle punctures said skin along said guide member.

(9) The puncture device according to aforesaid (8), characterized by being constituted in the dermis layer positioned on the lower side of said guide member such that said puncture needle is stuck in a state in which a tip portion including the needlepoint of said puncture needle becomes approximately parallel with respect to the body surface.

(10) The puncture device according to aforesaid (2), aforesaid (5) or aforesaid (8), characterized by being constituted such that said puncture needle moves on a turning trajectory having a predetermined turning radius, and the needlepoint of said puncture needle moves at least until the lowest point of said turning trajectory.

Also, the above-described object is accomplished also by the inventions of the following (11) to (22).

(11) The puncture device according to aforesaid (2), characterized in that there is formed on said puncture needle with a slit for mounting and dismounting said indwelling device.

(12) The puncture device according to aforesaid (2), characterized in that said indwelling device is a catheter.

(13) The puncture device according to aforesaid (5), characterized in that there is formed on said puncture needle with a slit for mounting and dismounting said indwelling device.

(14) The puncture device according to aforesaid (5), characterized in that said retaining member and said fixing member are constituted to be separable from each other.

(15) The puncture device according to aforesaid (5), characterized in that there is formed on said fixing member with a through-hole for retaining said indwelling device.

(16) The puncture device according to aforesaid (5), characterized in that said indwelling device is a catheter.

(17) The puncture device according to aforesaid (8), characterized in that said retaining member is a medicinal solution storage member having a liquid room which is in communication with said puncture needle.

(18) The puncture device according to aforesaid (8), characterized in that said retaining member is constituted by a fixing member fixing said puncture needle and a medicinal solution storage member detachable with respect to this fixing member.

(19) The puncture device according to aforesaid (8), characterized in that there is formed on said guide member with an insertion opening for inserting said puncture needle therethrough.

(20) The puncture device according to aforesaid (8), characterized in that there is formed on said guide member with a latch portion for latching said retaining member.

(21) The puncture device according to aforesaid (8), characterized in that there is formed on said guide member with a curved surface so as to be along the curvature of said puncture needle.

(22) In a puncture method puncturing a skin by a puncture needle, a puncture method using:
a device main body having a contact surface which contacts said skin;
a puncture needle having a curvature portion of a predetermined curvature radius; and
a puncture needle moving means provided in said device main body, characterized in that
said puncture needle is made by said puncture needle moving means to move along a circular trajectory which said curvature radius draws so as to puncture said skin.

EFFECT OF THE INVENTION

According to the present invention, it is possible for a puncture needle to reach a predetermined region certainly after being stuck from a skin.

Also, according to the present invention, it is possible by means of an indwelling device to inject a medical agent to a predetermined region of a skin certainly and also, it is possible to detect a predetermined substance in the skin.

BEST MODE FOR CARRYING OUT THE INVENTION

Hereinafter, it will be explained with respect to the best mode for practicing the puncture device of the present invention with reference to the drawings, wherein it should be noted that the present invention is not limited by the following modes.

FIRST EXEMPLIFIED EMBODIMENT

First, it will be explained with respect to a first exemplified embodiment of a puncture device of the present invention.

Figure 1:
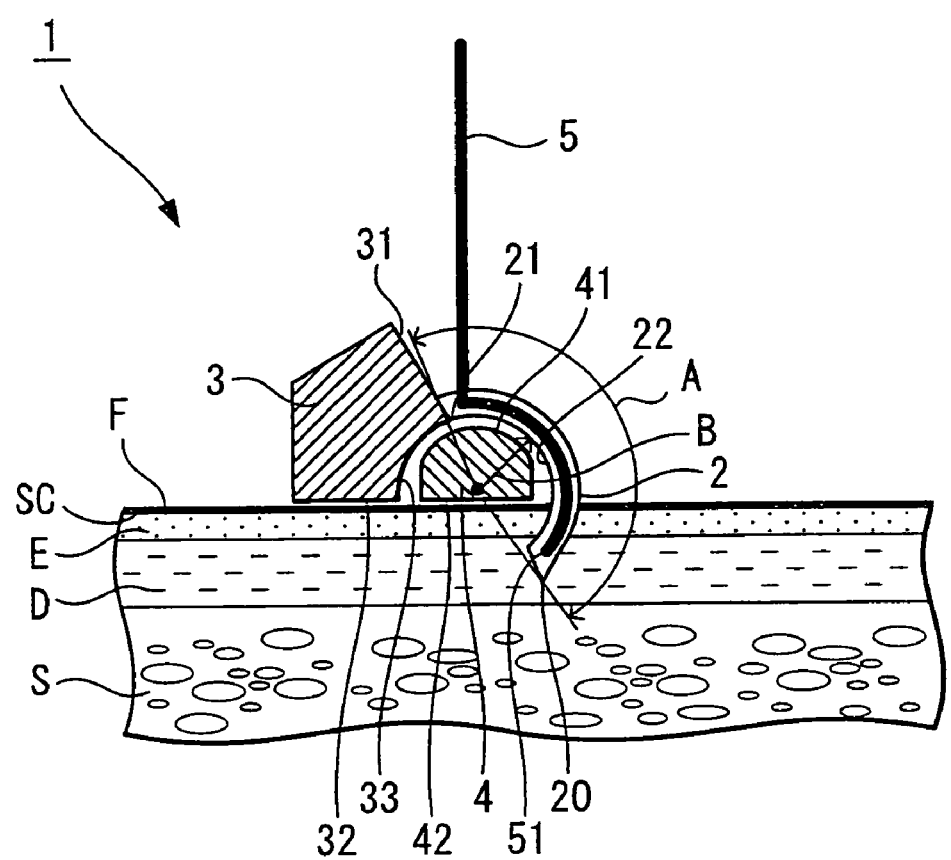
FIG. 1 shows a vertical cross-sectional view showing a first exemplified embodiment of a puncture device of the present invention.

FIG. 1 shows a vertical cross-sectional view showing a first exemplified embodiment of a puncture device of the present invention. Also, FIGS. 2A-2D are diagrams (vertical cross-sectional views) for explaining the usage of the puncture device shown in FIG. 1. It should be noted that it will be explained hereinafter on an assumption that the upside in FIG. 1 and FIG. 2 is made to be "rear end" and the downside thereof is made to be "tip".

A puncture device 1 shown in FIG. 1 has a puncture needle 2, a retaining member 3 retaining the puncture needle 2, a guide member 4 and a catheter (indwelling device) 5 inserted into the puncture needle 2.

The puncture needle 2 is a hollow needle which has a hollow portion inside and there are formed with a needlepoint 20 at the tip thereof and a coupling portion 21 being interlinked with the retaining member 3 at the rear end thereof.

Also, there is provided with a slit (not shown) for mounting and dismounting the catheter 5 along the longitudinal direction of the puncture needle. It should be noted for the shape of cross sectional of the puncture needle 2 provided with the slit that, for example, a lateral-U shape type or a vertical-U shape type in which the slit becomes an opening portion can be considered.

The puncture needle 2 has a curvature portion 22 and as shown in FIG. 1, the curvature portion 22 has a circular arc length A and a curvature radius B.

Although the outer diameter of the puncture needle 2 becomes a little bit different depending on the use application or the like of the puncture device 1, it is preferable to be around 0.05 mm to 2.0 mm and in particular it is preferable to be around 0.1 mm to 1.0 mm.

It is preferable for the circular arc length A of the curvature portion 22 to be set such that the central angle thereof is in a range of 45 to 180 degrees and although there is no limitation in particular, it is preferable for the curvature radius B to be around 1.0 to 5.0 mm.

For the constituent material of such the puncture needle 2, there can be cited, for example, a metal material such as stainless steel, aluminum or aluminum alloy, titanium or titanium alloy or the like. Also, the curvature portion 22 of the puncture needle 2 is manufactured, for example, by plastic working.

The retaining member 3 is constituted so as to include a mounting surface 31 for fixedly retaining the coupling portion 21 of the puncture needle 2, a skin contact surface 32 which will face to the body surface F immediately after the needlepoint 20 of the puncture needle 2 is stuck into the skin (body surface F), and a curved surface 33 which faces along a curved surface 41 of the guide member 4 to be described hereinafter.

It should be noted that it is desirable for the retaining member 3 to be provided with a grasp means such a grip or the like for improving operability by a user.

There can be cited for the constituent material of the retaining member 3 various kinds of resin materials such, for example, as polyethylene, polypropylene, polybutadiene, polyolefin such as ethylene-vinyl acetate copolymer, polyvinylchloride, polyurethane, polystyrene, polymethyl methacrylate, polycarbonate, polyamide, polyethylene terephthalate, polyester such as polybutylene terephthalate, acrylic resin, ABS resin, AS resin, ionomer, polyacetal, polyphenylene sulfide, polyether ether ketone and the like.

Also, the retaining member 3 is manufactured, for example, by such a molding process in which a resin material is to be inpoured in a die molded to have a desired shape.

Firm-fixation of the coupling portion 21 of the puncture needle 2 with respect to the retaining member 3 is accomplished, for example, by insert molding or adhesion. On this occasion, the coupling portion 21 of the puncture needle 2 is firmly fixed on the mounting surface 31 of the retaining member 3 such that the cross section curve of the curved surface 33 formed on the retaining member 3 and the curve on the inner side of the curvature portion 22 of the puncture needle 2 are to be connected.

By constituting in this manner, it is possible for a user to move the puncture needle 2 and the retaining member 3 smoothly along the curved surface 41 which the guide member 4 has, so that it is possible to improve operability when sticking the puncture device 2 into body surface F.

The guide member 4 is constituted so as to include the curved surface 41 for making the movement of the puncture needle 2 and the retaining member 3 to be smooth and a skin contact surface 42 having a plane for being fixed stably with respect to the skin S. This curved surface 41 is constituted so as to have such a shape of cross section along the curve of the curvature portion 22 of the puncture needle 2.

It should be noted that it is allowed to form a groove on the curved surface 41 so as to be along the shape of the curvature portion 22 of the puncture needle 2. By constituting in this manner, the movement of the puncture needle 2 is controlled and it is possible to puncture a correct position of the skin.

There can be cited for the constituent material of the guide member 4 various kinds of resin materials such, for example, as polyethylene, polypropylene, polybutadiene, polyolefin such as ethylene-vinyl acetate copolymer, polyvinylchloride, polyurethane, polystyrene, polymethyl methacrylate, polycarbonate, polyamide, polyethylene terephthalate, polyester such as polybutylene terephthalate, acrylic resin, ABS resin, AS resin, ionomer, polyacetal, polyphenylene sulfide, polyether ether ketone and the like.

Also, the guide member 4 is manufactured, for example, by such a molding process in which a resin material is inpoured into a die molded to be a desired shape.

The catheter 5 is inserted from the slit (not shown) formed on the puncture needle 2 into the hollow portion of the puncture needle 2. The catheter 5 has flexibility and has a medical agent supplying opening 51 at the tip portion thereof. Also, the catheter 5 is retained in the inside of the puncture needle 2 so as to be along the shape of the curvature portion 22. It should be noted that the medical agent supplying opening 51 of the catheter 5 may be provided at a portion other than the tip portion and in addition, it may be formed at a plurality of positions.

A liquid transmission pump (not shown) is connected to the edge portion of the catheter 5 and a medical agent is supplied from the medical agent supplying opening 51 into the skin.

It should be noted that the indwelling device inserted into the inside of the puncture needle 2 is not limited by the catheter supplying the medical agent, but it may be also allowed to employ a fiber cable catheter with a sensor, for example, a sensor for saccharide measurement provided with an optical fiber disclosed in Japanese Patent Laid-open No. H08-107890.

Also, in case of a sensor for saccharide measurement, it may be also allowed to employ a fluorescent sensor including a fluorescent dye composed of a phenyl boron derivative.

Also, in case of using a microdialysis sensor for the fiber cable catheter with a sensor, a portion of the catheter is formed by a dialysis membrane.

A measuring apparatus is connected to the edge portion of the catheter and a state in the skin is measured by the sensor. It should be noted in case of using the fluorescent sensor that a fluorescent measuring device is used for the measuring apparatus. Also, in case of using the microdialysis sensor, the measuring apparatus measures a substance to be measured in dialysate solution of the catheter.

Next, it will be explained by using FIG. 2 with respect to usage (operation) of the puncture device 1 of the first exemplified embodiment.

Figure 2A:
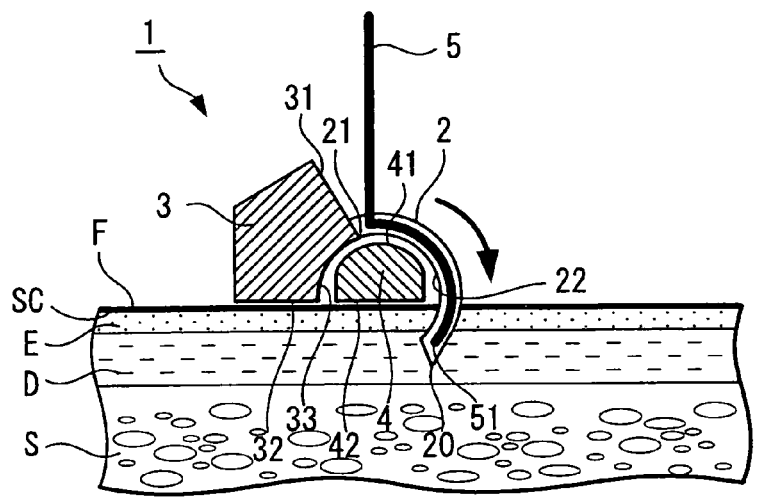
FIGS. 2A-2D are diagrams (vertical cross-sectional views) for explaining the usage of the puncture device shown in FIG. 1.

First, the retaining member 3 is grasped by fingers or the like and the puncture needle 2 and the retaining member 3 are turned so as to be along the guide member 4 to the direction of the arrow shown in FIG. 2A.

Figure 2B:
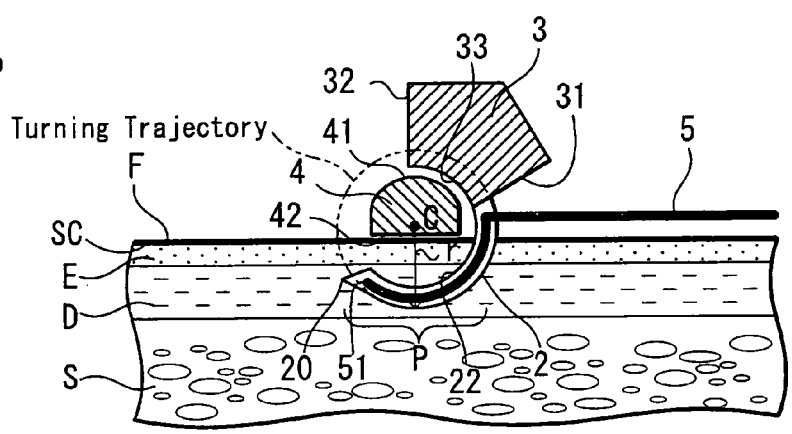

Thereby, the needlepoint 20 of the puncture needle 2 is stuck into the body in a state in which the puncture needle 2 is retaining the catheter 5 and as shown in FIG. 2B, the tip portion P of the puncture needle 2 including the needlepoint 20 is indwelled in the dermis D in such a state becoming approximately in parallel with the body surface F.

In this case, as shown in FIG. 2B, if the turning trajectory on which the puncture needle 2 moves is defined as a circular trajectory of turning radius r centering on a rotation center point c provided on the guide member 4, the puncture needle 2 is stuck after the needlepoint 20 of the puncture needle 2 is moved until it reaches at least the lowest point b of the circular trajectory. Further, preferably, the needlepoint 20 of the puncture needle 2 is made to move beyond the lowest point b and just before it reaches the upper surface of the dermis D.

More specifically, it is possible, by adjusting the magnitude of the turning radius r of the turning trajectory and the moving distance of the puncture needle 2, to carry out adjustment such that the needlepoint 20 of the puncture needle 2 is to be indwelled accurately in the dermis D.

At that time, when sticking the puncture needle 2 into the body, it is possible to insert the needlepoint 20 into the body by maintaining a state in which the curvature portion 22 of the puncture needle 2 is to lift the skin, so that it is possible for a user to carry out the puncture operation by means of the puncture needle easily and certainly.

Also, by adjusting the circular arc length A of the curvature portion 22 or the curvature radius B to be a predetermined length, it is possible to indwell the needlepoint 20 of the puncture needle 2 certainly in the dermis D.

Figure 2C:
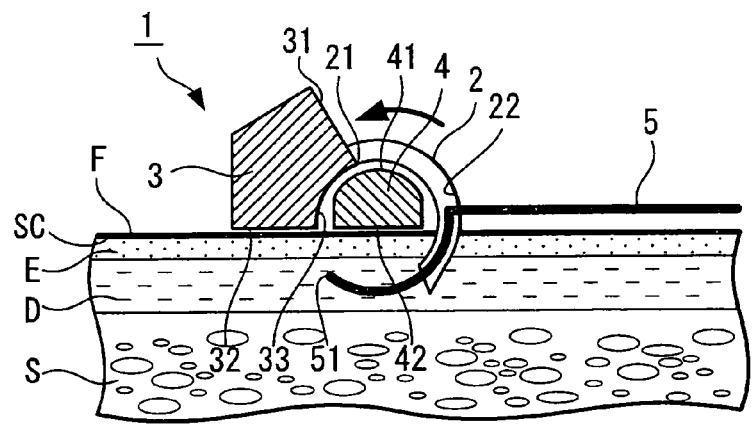

Next, the retaining member 3 is grasped again by fingers or the like and the puncture needle 2 and the retaining member 3 are turned so as to be along the guide member 4 to the direction of the arrow shown in FIG. 2C.

Figure 2D:
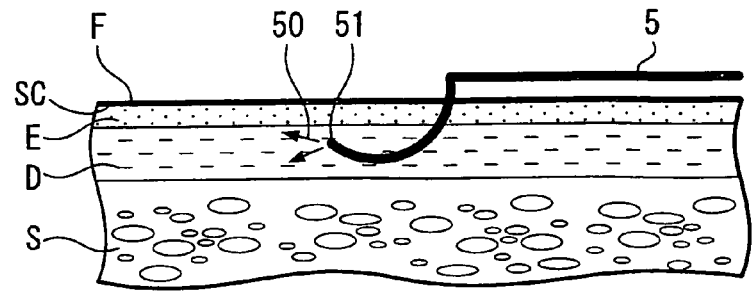

Thereby, the catheter 5 is separated from the slit formed on the puncture needle 2 and as shown in FIG. 2D, the catheter 5 including the medical agent supplying opening 51 is indwelled in the dermis D in the body. In this state, a medical agent such as insulin, growth hormone or the like is supplied from the liquid transmission pump and the medical agent 50 is supplied from the medical agent supplying opening 51 to the dermis D.

In this manner, according to the puncture device 1 of this exemplified embodiment, the puncture needle 2 is stuck certainly into the dermis D, so that it is possible to indwell the catheter in the dermis D and it is possible to inject the medical agent certainly into the dermis D.

Also, according to the puncture device 1 of this exemplified embodiment, the puncture needle 2 is stuck in a condition that the puncture needle 2 becomes in a state approximately in parallel with respect to the body surface F within the dermis D, so that the insertion depth of the puncture needle 2 in the inside of the dermis D becomes long and even in a case in which an impact or the like is added from the outside, the catheter 5 during injecting the medical agent can be prevented from dropping out from the dermis D.

Further, the distance from the insertion aperture of the catheter 5, which is formed at a boundary portion between the epidermis E and the dermis D until the medical agent supplying opening 51 becomes long, so that the medical agent once injected into the dermis D from the medical agent supplying opening 51 can be prevented from leaking from the insertion aperture to the epidermis E by being flown back.

SECOND EXEMPLIFIED EMBODIMENT

Next, it will be explained with respect to a second exemplified embodiment of a puncture device of the present invention.

Figure 3:
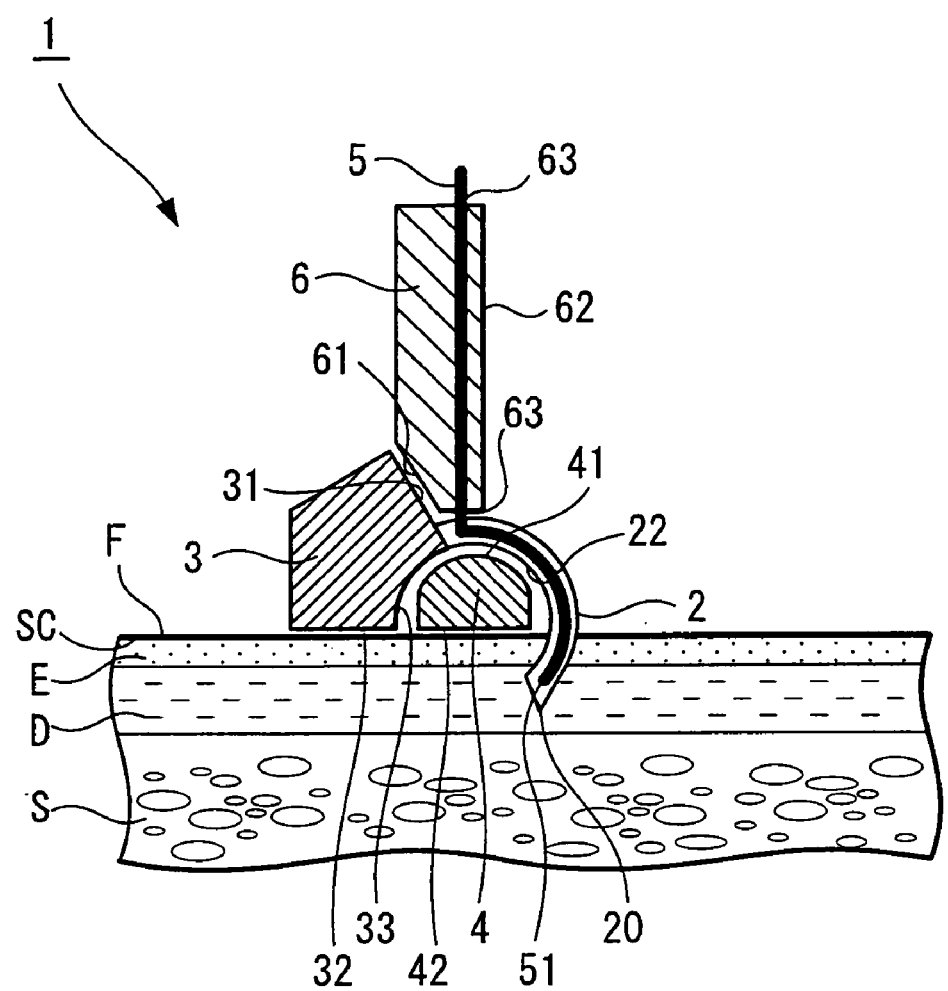
FIG. 3 is a vertical cross-sectional view showing a second exemplified embodiment of a puncture device of the present invention.

FIG. 3 is a vertical cross-sectional view showing a second exemplified embodiment of a puncture device of the present invention. Also, FIGS. 4A-4D are diagrams (vertical cross-sectional views) for explaining the usage of the puncture device shown in FIG. 3. It should be noted that it will be explained hereinafter on an assumption that the upside in FIG. 3 and FIG. 4 is made to be "rear end" and the downside thereof is made to be "tip".

Hereinafter, it will be explained with respect to the puncture device of the second exemplified embodiment centering on differences from the puncture device of aforesaid first exemplified embodiment and with respect to similar matters, the explanations thereof will be omitted.

The puncture device 1 of the second exemplified embodiment is provided with a fixing member 6 for fixedly retaining the catheter 5 so a to be separable with respect to the retaining member 3, and the rest thereof is similar as the puncture device 1 of the aforesaid first exemplified embodiment.

The fixing member 6 is constituted so as to include an engagement surface 61 which is engaged separably with the mounting surface 31 of the retaining member 3 and a skin contact surface 62 having a plane for being fixed stably with respect to the body surface F. It should be noted that the skin contact surface 62 is formed by a plane having an area as large as possible in order to improve the stability.

It is allowed as a constitution making the retaining member 3 and the fixing member 6 to be separable to employ, for example, a constitution in which the mounting surface 31 of the retaining member 3 and the engagement surface 61 are made to be separable by pasting an adhesive tape having weak adherence on the engagement surface 61. Also, it is be allowed to employ a constitution in which a convex portion is provided on the retaining member 3 and the retaining member 3 and the fixing member 6 are made to be separable by providing on the fixing member 6 with a concave portion engageable with that convex portion.

Also, the fixing member 6 is formed with a through-hole 63 for inserting the catheter 5 in the longitudinal direction of the retaining member 6 and in the direction in parallel with the skin contact surface 62.

Thereby, when the catheter 5 is indwelled in the body, the portion of the catheter 5 arranged on the inside and on the outside of the body can be retained and fixed so as to be in parallel with respect to the body surface F. Accordingly, the medicinal solution to be supplied into the body through the catheter 5 can be supplied in a stable state without clogging.

There can be cited for the constituent material of the fixing member 6 various kinds of resin materials such, for example, as polyethylene, polypropylene, polybutadiene, polyolefin such as ethylene-vinyl acetate copolymer, polyvinylchloride, polyurethane, polystyrene, polymethyl methacrylate, polycarbonate, polyamide, polyethylene terephthalate, polyester such as polybutylene terephthalate, acrylic resin, ABS resin, AS resin, ionomer, polyacetal, polyphenylene sulfide, polyether ether ketone and the like.

Also, the fixing member 6 is manufactured, for example, by such a molding process in which a resin material is inpoured into a die molded to be a desired shape.

Next, it will be explained by using FIG. 4 with respect to usage (operation) of the puncture device 1 of the second exemplified embodiment.

Figure 4A:
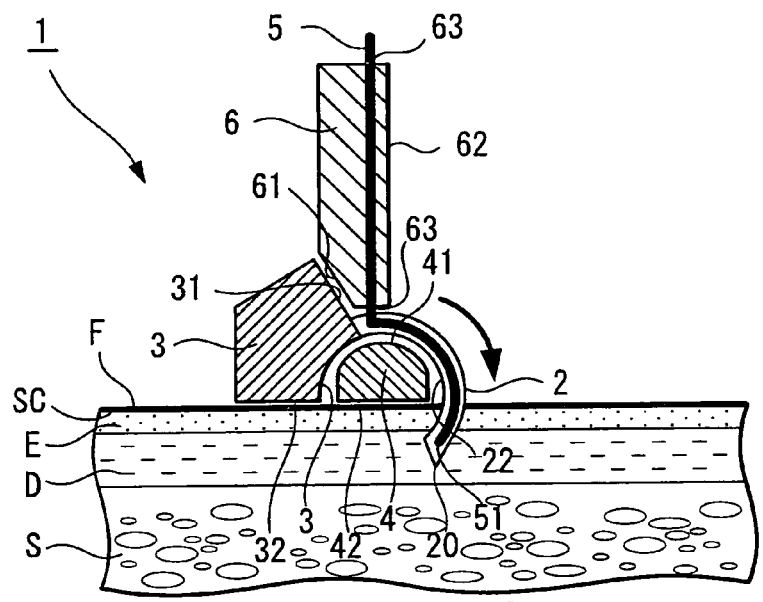
FIGS. 4A-4D are diagrams (vertical cross-sectional views) for explaining the usage of the puncture device shown in FIG. 3.

First, the retaining member 3 is grasped by fingers or the like and the puncture needle 2, the retaining member 3 and the fixing member 6 in a state being engaged with the retaining member 3 are turned so as to be along the guide member 4 to the direction of the arrow shown in FIG. 4A. It should be noted that the fixing member 6 is engaged with the retaining member 3 in such a state in which the engagement surface 61 is to be faced to the mounting surface 31 of the retaining member 3.

Figure 4B:
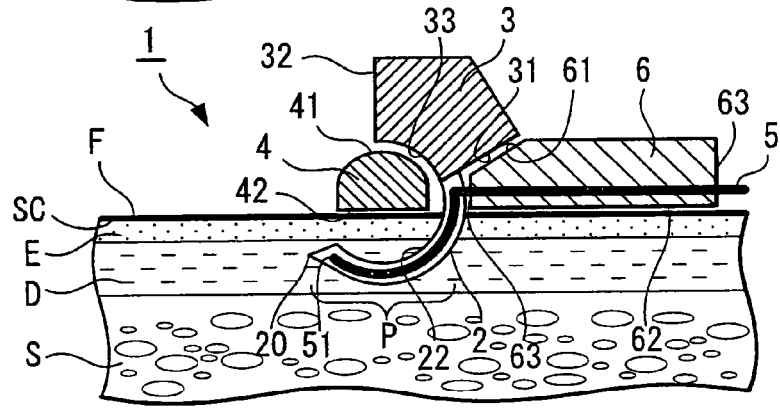

Thereby, the needlepoint 20 of the puncture needle 2 is stuck into the body in a state in which the puncture needle 2 and the fixing member 6 are retaining the catheter 5 in the inside thereof and as shown in FIG. 4B, the tip portion P of the puncture needle 2 including the needlepoint 20 is indwelled in the dermis D in such a state becoming approximately in parallel with the body surface F.

Figure 4C:
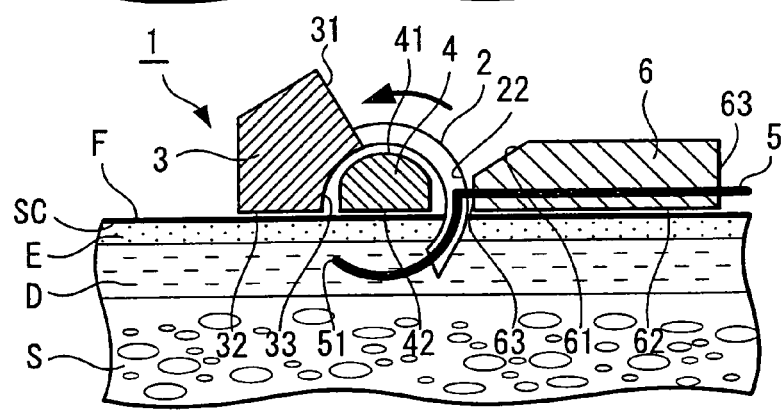

Next, the retaining member 3 is grasped again by fingers or the like and the puncture needle 2 and the retaining member 3 are turned so as to be along the guide member 4 to the direction of the arrow shown in FIG. 4C. Thereby, the engagement between the mounting surface 31 of the retaining member 3 and the engagement surface 61 of the fixing member 6 is unfastened, the retaining member 3 and the fixing member 6 are separated from each other, and the fixing member 6 maintains the state of being mounted on the body surface F.

Figure 4D:
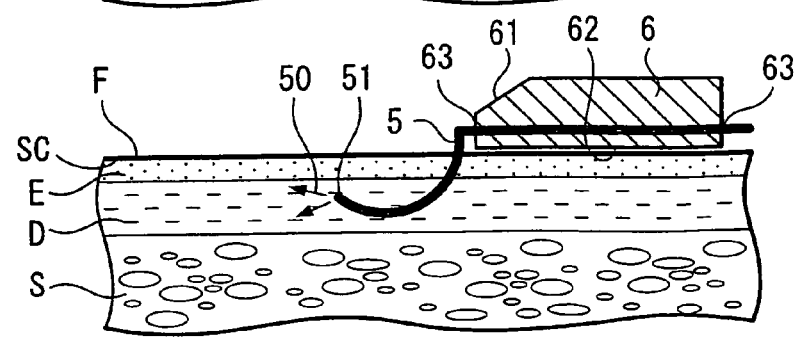

Along with the turning operation, the catheter 5 is separated from the slit formed on the puncture needle 2 and as shown in FIG. 4D, the catheter 5 including the medical agent supplying opening 51 is indwelled in the dermis D in the body and at the same time, the catheter 5 of the portion arranged on the outside of the body is retained and fixed by the fixing member 6 so as to become horizontal with respect to the body surface F. In this state, a medical agent is supplied from the liquid transmission pump connected to the catheter 5 and the medical agent 50 is supplied from the medical agent supplying opening 51 to the dermis D.

In this manner, according to the puncture device 1 of this exemplified embodiment, the puncture needle 2 is stuck certainly into the dermis D, so that it is possible to indwell the catheter in the dermis D certainly. Accordingly, it is possible to inject the medical agent certainly into the dermis D.

Also, it is possible by the fixing member 6 to maintain the catheter 5 during supplying the medical agent in a stable state, so that it is possible to supply the medical agent certainly.

Also, according to the puncture device 1 of this exemplified embodiment, the puncture needle 2 is stuck in a condition that the puncture needle 2 becomes in a state approximately in parallel with respect to the body surface F within the dermis D, so that the insertion depth of the puncture needle 2 in the inside of the dermis D becomes long and even in a case in which an impact or the like is added from the outside, the catheter 5 during injecting the medical agent can be prevented from dropping out from the dermis D.

Further, the distance from the insertion aperture of the catheter 5, which is formed at a boundary portion between the epidermis E and the dermis D until the medical agent supplying opening 51 becomes long, so that the medical agent once injected into the dermis D from the medical agent supplying opening 51 can be prevented from leaking from the insertion aperture to the epidermis E by being flown back.

THIRD EXEMPLIFIED EMBODIMENT

Next, it will be explained with respect to a third exemplified embodiment of a puncture device of the present invention.

Figure 5:
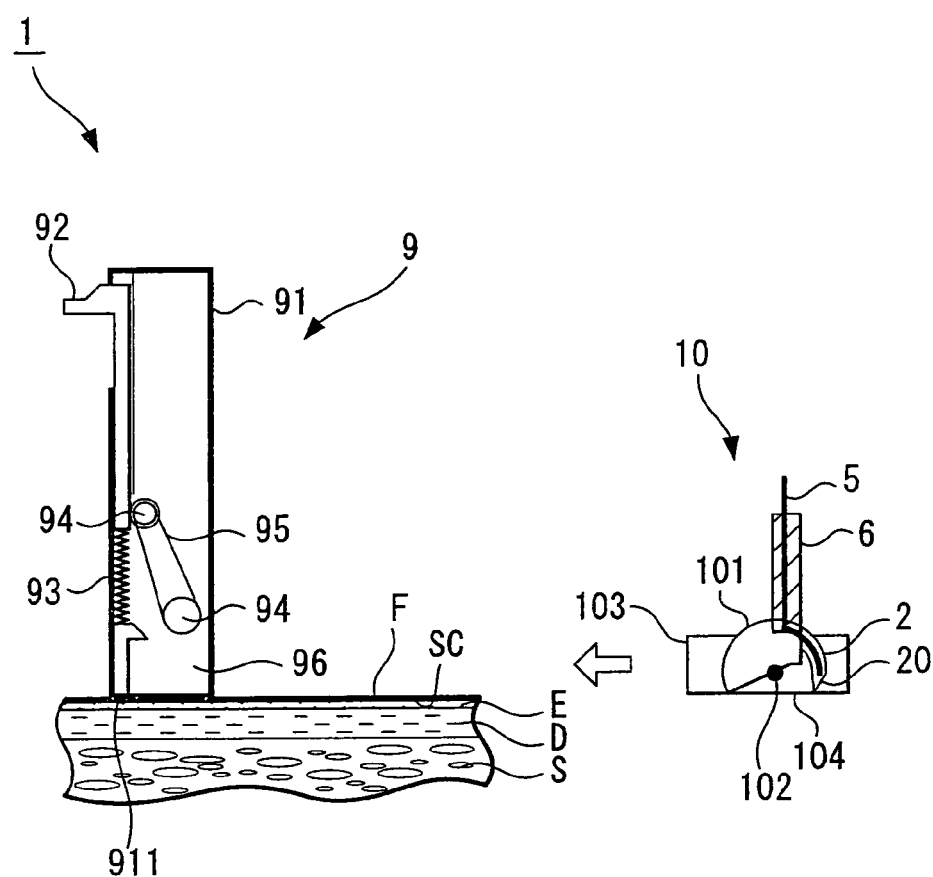
FIG. 5 is a vertical cross-sectional view showing a third exemplified embodiment of a puncture device of the present invention.

FIG. 5 is a vertical cross-sectional view of a setting device 9 and a disposable cassette 10 constituting a puncture device 1 of this exemplified embodiment. Also, FIGS. 6A-6D are diagrams (vertical cross-sectional views) for explaining the usage of the puncture device shown in FIG. 5. It should be noted that it will be explained hereinafter on an assumption that the upside in FIG. 5 is made to be "rear end" and the downside thereof is made to be "tip".

The setting device 9 as a device main body shown in FIG. 5 is constituted by an outer frame 91, a lever 92 mounted on the outer frame 91 to be movable, an elastic member 93 mounted on the lever 92, a pair of rollers 94 provided in the inside of the outer frame 91 and retained therein to be rotatable, and a belt 95 winded around these pair of rollers 94.

The setting device 9 is formed with a mounting portion 96 for mounting the disposable cassette 10 in the inside thereof. Also, there is formed on the body surface F side of the outer frame 91 with a skin contact surface 911 for contacting with the skin.

The disposable cassette 10 shown in FIG. 5 is constituted by a catheter 5, a fixing member 6 retaining this catheter 5 in the inside, a half round plate member 101 retaining the fixing member 6 detachably, a rotation axis 102 supporting the half round plate 101 rotatably, and an outer frame 103 on which the rotation axis 102 is fixed.

The half round plate 101 is mounted along the circumference of the circular plate with a puncture needle 2 having predetermined curvature radius and circular arc. At that time, a needlepoint 20 of the puncture needle 2 is mounted so as to be adjacent to the body surface F.

The half round plate 101 is supported by the outer frame 103 so as to be able to turn in the inside of the outer frame 103 centering on the rotation axis 102. Also, there is formed on the body surface F side of the outer frame 103 with a skin contact surface 104 for contacting with the skin.

Next, it will be explained by using FIG. 6 with respect to usage (operation) of the puncture device 1 of the third exemplified embodiment.

Figure 6A:
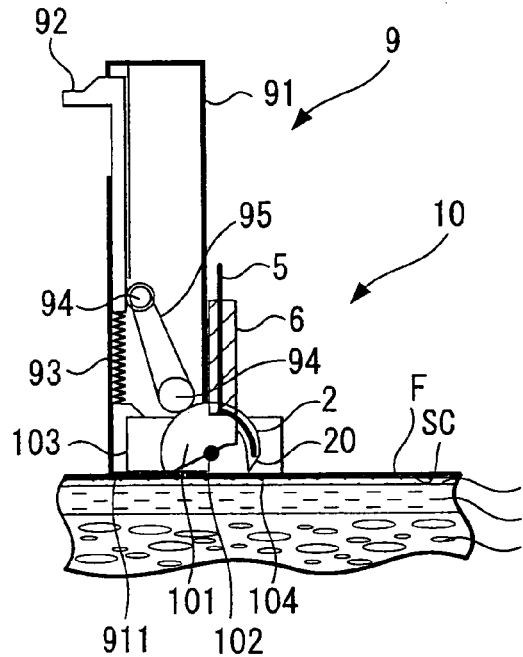
FIGS. 6A-6D are diagrams (vertical cross-sectional views) for explaining the usage of the puncture device shown in FIG. 5.

First, as shown in FIG. 6A, the puncture device 1 is mounted on the skin in a state in which the disposable cassette 10 is mounted on the mounting portion 95 of the setting device 9. At that time, the puncture device 1 is mounted on the skin such that the skin contact surface 911 of the setting device 9 and the skin contact surface 104 of the disposable cassette 10 are to be attached closely onto the body surface F.

Also, when the disposable cassette 10 is mounted on the setting device 9, the mounting thereof is carried out such that the tip side roller 94 provided in the inside of the setting device 9 and the half round plate 101 of the disposable cassette 10 will contact with each other.

Figure 6B:
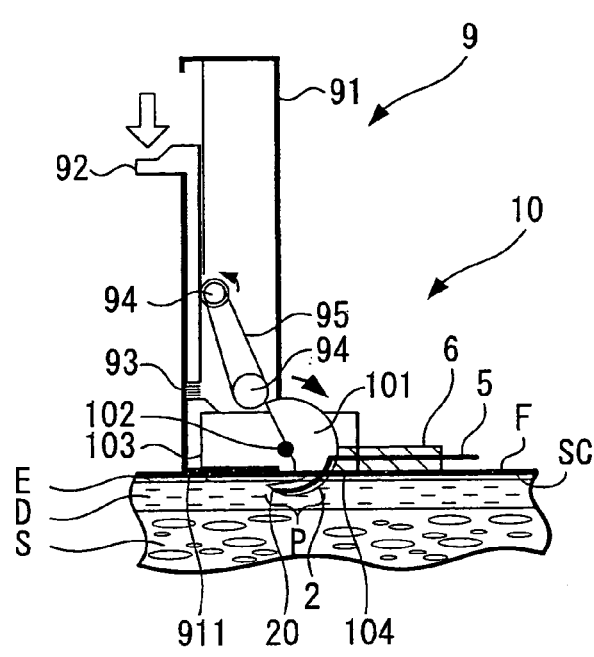

Next, as shown in FIG. 6B, the lever 92 of the setting device 9 is pushed down against the resistance of the elastic member 93 toward the tip side. Thereby, the roller 94 on the rear end side and contacting with the lever 92 rotates.

When the roller 94 on the rear end side rotates, the roller 94 on the tip side rotates through the belt 95. When the roller 94 on the tip side rotates, the half round plate 101 contacting with this roller 94 turns centering on the rotation axis 102.

When the half round plate 101 turns, also the puncture needle 2 mounted on the half round plate 101 turns and the needlepoint 20 of the puncture needle 2 is stuck into the skin.

In addition, concurrently with this, also the fixing member 6 mounted on the half round plate 101 turns toward the body surface F.

Further, when the lever 92 is pushed down to the tip side, the half round plate 101 turns further and as shown in FIG. 6B, the tip portion P of the puncture needle 2 including the needle-point 20 is indwelled in the dermis D in a state being approximately in the horizontal direction with respect to the body surface F. Also, concurrently with this, the skin contact surface 62 of the fixing member 6 is to be mounted on the skin so as to be attached closely to the body surface F.

Figure 6C:
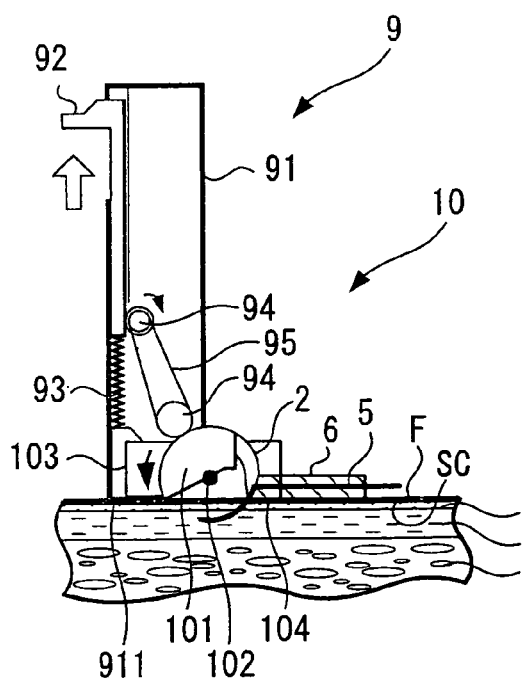

Next, as shown in FIG. 6C, the lever 92 of the setting device 9 is pulled up to the rear end side. In this case, by releasing the force added to the lever 92, the lever 92 is pulled up automatically to the rear end side owing to the elastic force of the elastic member 93.

Thereby, the roller 94 on the rear end side, which contacts with the lever 92 rotates in the opposite direction compared with the case in which the lever 92 is pushed down.

When the roller 94 of the rear end side rotates to the opposite direction, the roller 94 on the tip side rotates also to the opposite direction. When the roller 94 on the tip side rotates to the opposite direction, the half round plate 101 also turns to the opposite direction.

Thereby, the puncture needle 2 mounted on the half round plate 101 is pulled out from the skin. Concurrently with this, the catheter retained by the puncture needle 2 is unfastened from the slit provided on the puncture needle 2 and indwelled in the dermis D.

Also, when the half round plate 101 turns to the opposite direction, the fixing member 6 which was mounted on the half round plate 101 detachably is separated from the half round plate 101.

Figure 6D:
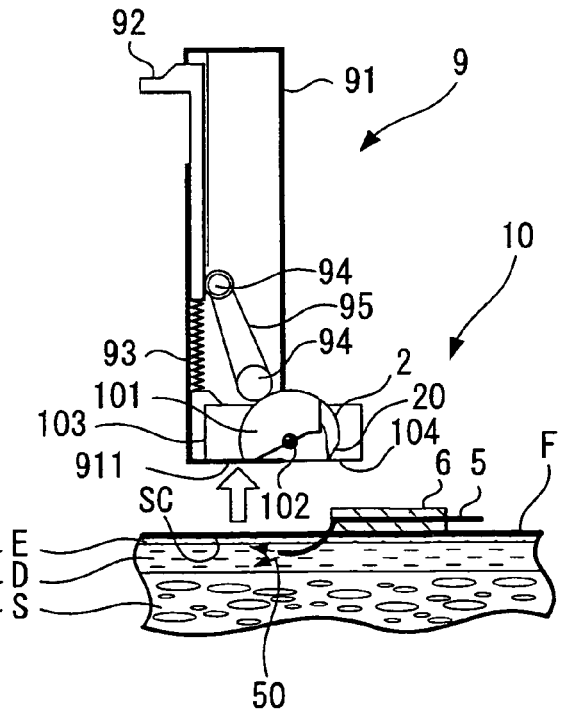

Next, as shown in FIG. 6D, the puncture device 1 is separated from the body surface F, and the setting device 9 and the disposable cassette 10 excluding the fixing member 6 are discarded integrally. At that time, the puncture needle 2 is housed in the inside of the outer frame 103 of the disposable cassette 10 other than the occasion of puncture, so that it is effective for the prevention of contamination or infection.

As shown in FIG. 6D, a medical agent is administered to the dermis D from a liquid transmission pump (not shown) connected to the edge of the catheter 5 in a state in which the catheter 5 is indwelled in the dermis D. It should be noted that in case of indwelling not the catheter 5 but a fiber cable catheter with a sensor in the dermis D, the state of the dermis D is to be measured by using a measuring apparatus connected to the edge of the catheter.

In this manner, according to the puncture device 1 of this exemplified embodiment, it is certainly possible to stick the puncture needle 2 into the dermis D and to indwell the catheter in the dermis D certainly. More specifically, it is possible to inject the medical agent certainly into the dermis D.

Also, the puncture by the puncture needle 2 is carried out mechanically, so that it is possible to stick the puncture needle 2 into the dermis D more certainly.

Also, according to the puncture device 1 of this exemplified embodiment, the puncture needle 2 is stuck in a condition that the puncture needle 2 becomes in a state approximately in parallel with respect to the body surface F within the dermis D, so that the insertion depth of the puncture needle 2 in the inside of the dermis D becomes long and even in a case in which an impact or the like is added from the outside, the catheter 5 during injecting the medical agent can be prevented from dropping out from the dermis D.

Further, the distance from the insertion aperture of the catheter 5, which is formed at a boundary portion between the epidermis E and the dermis D until the medical agent supplying opening 51 becomes long, so that the medical agent once injected into the dermis D from the medical agent supplying opening 51 can be prevented from leaking from the insertion aperture to the epidermis E by being flown back.

FOURTH EXEMPLIFIED EMBODIMENT

Next, it will be explained with respect to a fourth exemplified embodiment of a puncture device of the present invention.

Figure 7:
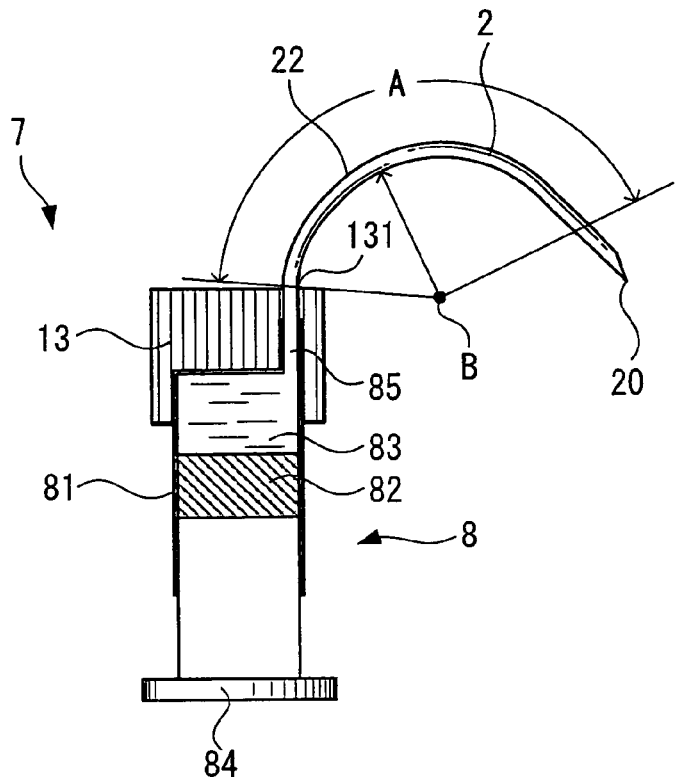
FIG. 7 is a vertical cross-sectional view of an injector device 7 used in this exemplified embodiment.

FIG. 7 is a vertical cross-sectional view of an injector device 7 to be used in this exemplified embodiment.

An injector device 7 shown in FIG. 7 includes a puncture needle 2, a hub (retaining member) 13 retaining the puncture needle 2, and a syringe 8.

The puncture needle 2 is a hollow needle having a hollow portion inside and is formed with a needlepoint 20 at the tip, and the rear end thereof is coupled with the hub 13.

The puncture needle 2 has a circular arc shaped curvature portion 22 and the curvature portion 22 has, as shown in FIG. 7, a circular arc length A and a curvature radius B.

Although the outer diameter of the puncture needle 2 becomes a little bit different depending on the use application or the like of the puncture device 1, it is preferable to be around 0.05 mm to 2.0 mm and in particular it is preferable to be around 0.1 mm to 1.0 mm.

It is preferable for the circular arc length A of the curvature portion 22 to be set such that the central angle thereof becomes in a range of 45 to 150 degrees and although there is no limitation in particular, it is preferable for the curvature radius B to be around 1.0 to 5.0 mm.

For the constituent material of such the puncture needle 2, there can be cited, for example, a metal material such as stainless steel, aluminum or aluminum alloy, titanium or titanium alloy or the like. Also, the curvature portion 22 of the puncture needle 2 is manufactured, for example, by plastic forming.

The hub 13 is constituted by a tubular member with a bottom and there is formed on a portion of a circumference edge portion of the bottom portion with an opening 131 for inserting the puncture needle 2, and the puncture needle 2 is fixed in the opening 131 thereof adhesively.

Also, the hub 13 is mounted with a syringe (medicinal solution storage member) 8 detachably.

The syringe 8 is provided with an external cylinder 81, a gasket 82 slidable in the external cylinder 81, and a plunger 84 operating the gasket 82. The external cylinder 81 is constituted by a tubular member with a bottom and there is formed on a portion of the circumference edge portion of the bottom portion with a through-hole 85 which can be in communication with the hollow portion of the puncture needle 2 by being coincident with the opening 131 provided on the hub 13.

Also, in the space surrounded by the external cylinder 81 and the gasket 82, a liquid room 83 is formed and liquid is contained liquid-tightly beforehand.

When using the syringe 8, sealing is released by exfoliating and removing a seal member of a film or the like from the tip of the through-hole 85 and the hub 13 is mounted on the syringe 8 after making the opening 131 formed on the hub 13 and the through-hole 85 formed in the syringe 8 to coincide with each other.

Subsequently, the plunger 84 is depressed to the tip direction, the gasket 82 coupled with the plunger 84 slides in the external cylinder 81 to the tip direction, and the liquid in the liquid room 83 is exhausted into the body after passing through the through-hole 85 and the hollow portion of the puncture needle 2.

It should be noted in this exemplified embodiment that a constitution in which the syringe 8 is detachable with respect to the hub 13 was employed, but it may be a constitution in which the hub 13 and the external cylinder 81 of the syringe 8 are formed as one body configuration.

Figure 8:
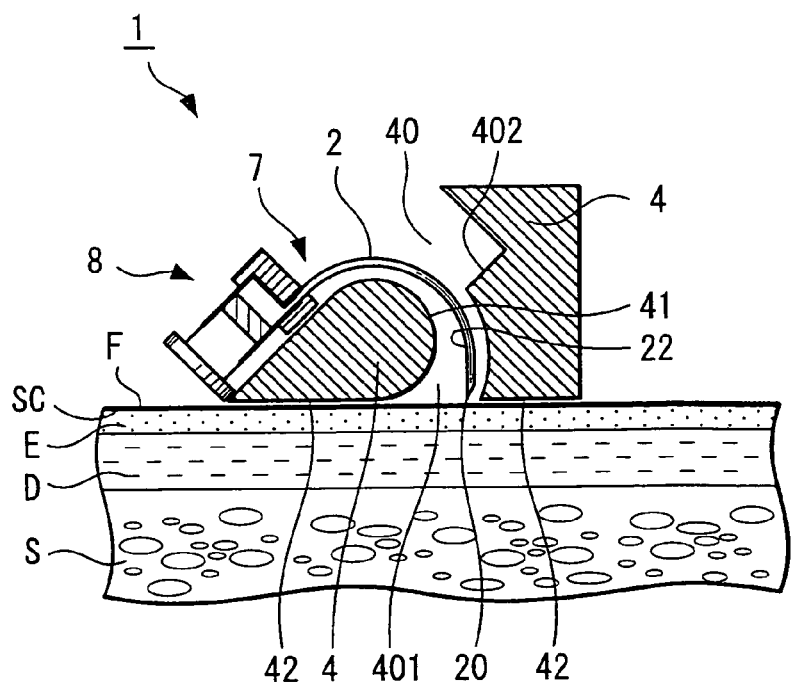
FIG. 8 is a vertical cross-sectional view showing a fourth exemplified embodiment of a puncture device of the present invention.

FIG. 8 is a vertical cross-sectional view showing a third exemplified embodiment of a puncture device of the present invention.

Also, FIGS. 9A-9D are diagrams (vertical cross-sectional views) for explaining the usage of the puncture device shown in FIG. 8.

As shown in FIG. 8, the puncture device of this exemplified embodiment is constituted by an injector device 7 and a guide member 4.

The guide member 4 is formed with an insertion portion 40 for inserting the injector device 7. The insertion portion 40 is formed with an insertion opening 401 for inserting the puncture needle 2 of the injector device 7 and a latch portion 402 for controlling the movement of the injector device 7 by being engaged with a portion of the external cylinder 81 of the syringe 8.

The latch portion 402 is formed to have such a shape to coincide with the outer shape of the syringe 8.

In order to make the movement of the puncture needle 2 to be smooth, the insertion opening 401 is formed to be such a shape being along the curve of the curvature portion 22 of the puncture needle 2. Thereby, it is possible to move the injector device 7 smoothly along the guide member 4, so that it is possible to improve operability of the puncture device 1 when puncturing the body surface F.

Also, there is formed on the side of the guide member 4 facing to the body surface F with a skin contact surface 42 having a plane for the guide member 4 to maintain a stable state with respect to the skin.

There can be cited for the constituent material of the guide member 4 various kinds of resin materials such, for example, as polyethylene, polypropylene, polybutadiene, polyolefin such as ethylene-vinyl acetate copolymer, polyvinylchloride, polyurethane, polystyrene, polymethyl methacrylate, polycarbonate, polyamide, polyethylene terephthalate, polyester such as polybutylene terephthalate, acrylic resin, ABS resin, AS resin, ionomer, polyacetal, polyphenylene sulfide, polyether ether ketone and the like.

Also, the guide member 4 is manufactured, for example, by a molding process in which a resin material is inpoured into a die molded to be a desired shape.

Next, it will be explained by using FIG. 9 with respect to usage (operation) of the puncture device 1 of the fourth exemplified embodiment.

Figure 9A:
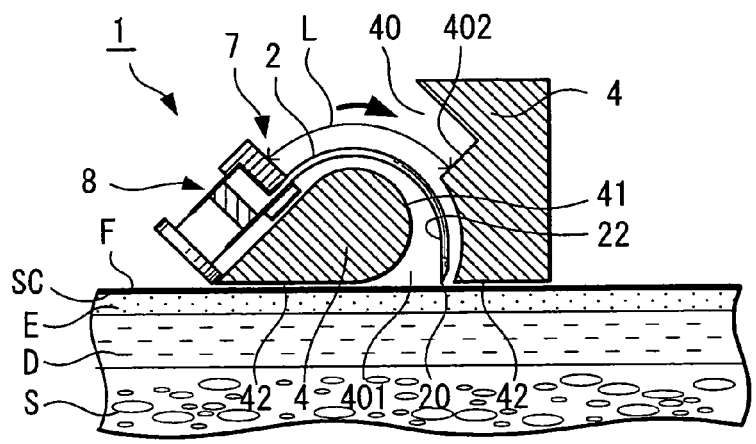
FIGS. 9A-9D are diagrams (vertical cross-sectional views) for explaining the usage of the puncture device shown in FIG. 8.

First, the syringe 8 is grasped by fingers or the like and the injector device 7 is turned so as to be along the guide member 4 to the direction of the arrow shown in FIG. 9A.

Figure 9B:
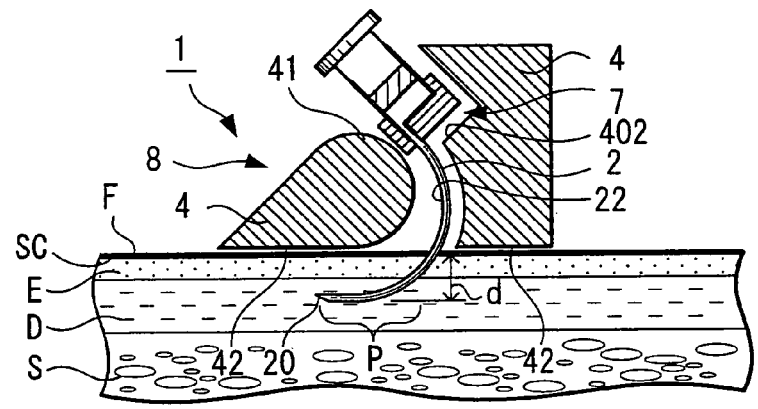

Then, a portion of the syringe 8 is latched on the latch portion 402 provided in the guide member 4 and as shown in FIG. 9B, the tip portion P of the puncture needle 2 including the needlepoint 20 is indwelled in the body in a state approximately in parallel with the body surface F. More specifically, the tip portion P of the puncture needle is stuck into the dermis D positioned on the lower side of the skin contact surface 42 of the guide member 4 in a state maintaining approximately a horizontal state with respect to the body surface F.

In this case, the insertion depth of the puncture needle 2 inserted into the body is determined by the circular arc length L from the latch portion 402 until the syringe 8 when the injector device 7 as shown in FIG. 9A is set in the guide member 4.

In other words, by adjusting the position of the latch portion 402 provided in the guide member 4, it is possible to place the needlepoint 20 of the puncture needle 2 certainly in the dermis D. Similarly, by adjusting the circular arc length A or the curvature radius B of the curvature portion 22 to become a predetermined length, it is possible to indwell the needlepoint 20 of the puncture needle 2 certainly in the dermis D.

It should be noted at that time that it is possible to insert the needlepoint 20 into the body by maintaining a state in which the curvature portion 22 of the puncture needle 2 lifts the skin, so that it is possible for a user to carry out the puncture operation by means of the puncture needle easily and also certainly.

Figure 9C:
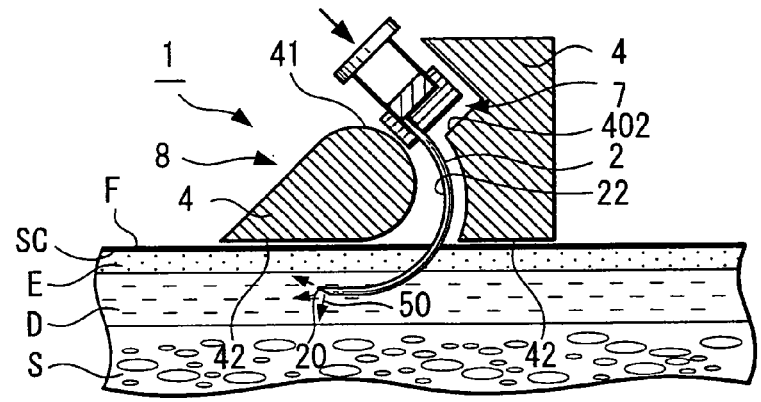

Next, as shown in FIG. 9C, by depressing the plunger 84 of the syringe 8, the medical agent 50 is injected from the tip of the puncture needle 2 into the dermis D.

Figure 9D:
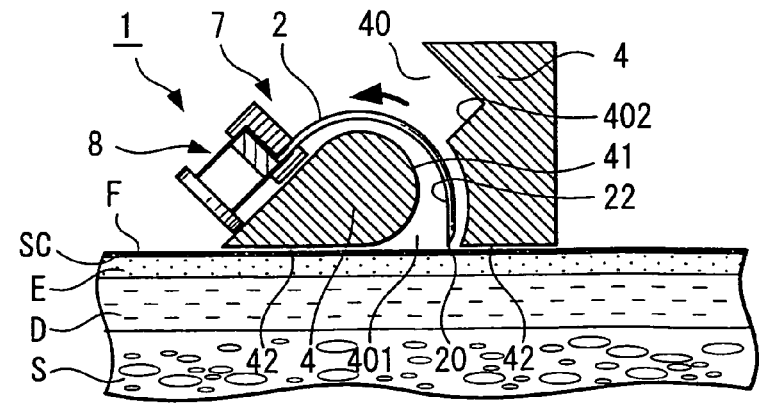
Figure 10:
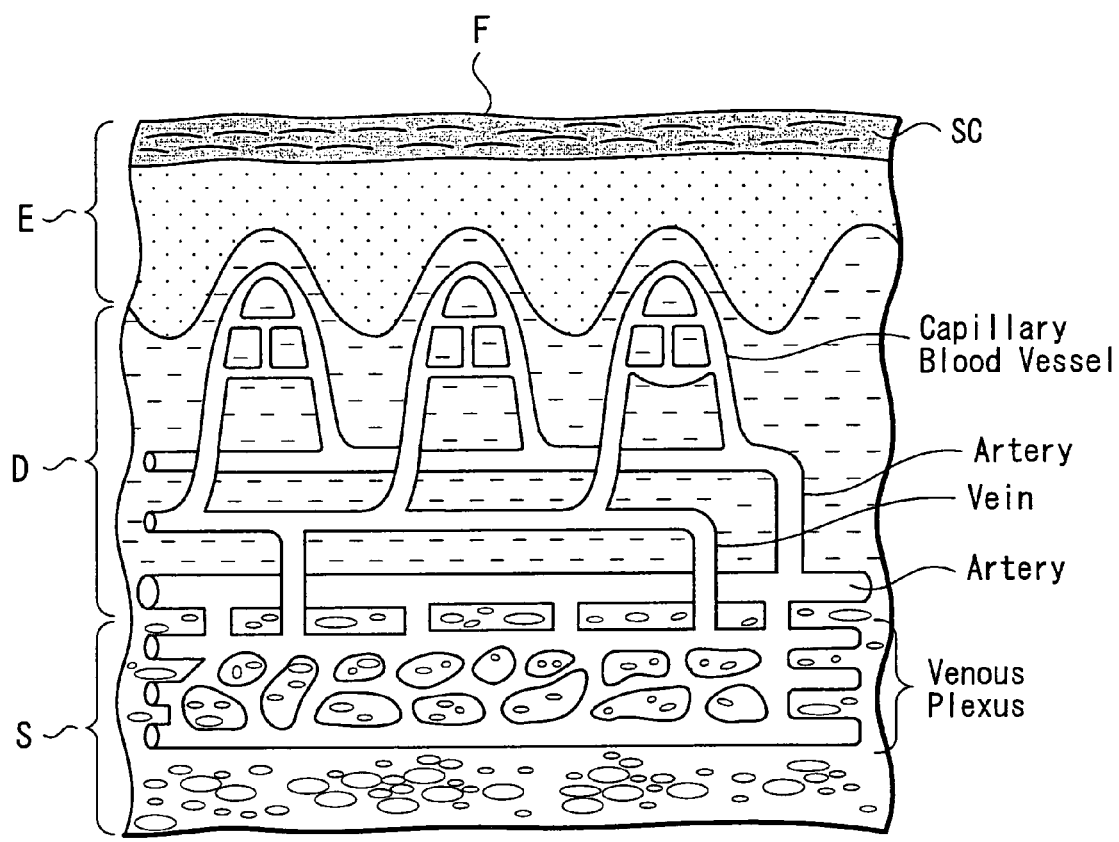
FIG. 10 is a view showing a cross-section structure of a general skin.

Next, the syringe 8 is grasped again by fingers or the like and the puncture needle 2 is pulled out from the body by turning the injector device 7 to the direction of the arrow shown in FIG. 9D so as to be along the guide member 4.

In this manner, according to the puncture device 1 of this exemplified embodiment, it is possible to stick the puncture needle 2 into the dermis D certainly, so that it is possible to inject a medical agent into the dermis D certainly.

Also, according to the puncture device 1 of this exemplified embodiment, the puncture needle 2 is stuck in a condition that the puncture needle 2 becomes in a state approximately in parallel with respect to the body surface F within the dermis D, so that the insertion depth of the puncture needle 2 in the inside of the dermis D becomes long and even in a case in which an impact or the like is added from the outside, the catheter 5 during injecting the medical agent can be prevented from dropping out from the dermis D.

Further, the distance from the insertion aperture of the puncture needle 2, which is formed at a boundary portion between the epidermis E and the dermis D until the needlepoint 20 becomes long, so that the medical agent once injected into the dermis D from the needlepoint 20 can be prevented from leaking from the insertion aperture to the epidermis E by being flown back.

It should be noted in the above-described exemplified embodiments that it was explained by using exemplified examples in which the puncture needle is always stuck to the dermis D, but it is possible to use the puncture device of the present invention also in case of puncturing an intracutaneous area, a subcutis or further a muscle other than the dermis.

It should be noted that the puncture device of the present invention is not limited by the above-mentioned each exemplified embodiment and besides that, it goes without saying that various modifications or changes can be employed for the materials, the constitutions or the like in the region without departing from the configuration of the present invention.

The invention claimed is:

1. A puncture device for puncturing a skin by a puncture needle, the puncture device comprising:
    a device main body having a contact surface which contacts said skin;
    a puncture needle having a needlepoint and a curvature portion curved along the lengthwise direction of the puncture needle and possessing a predetermined curvature radius; an indwelling device configured to be indwelled in a living body by said puncture needle; and a puncture needle moving means provided in said device main body for moving said puncture needle along a circular trajectory which said curvature radius draws so that the puncture needle punctures said skin, wherein the puncture device is configured to prevent the needlepoint from protruding out of a surface of the skin while the puncture needle punctures the skin.

2. A puncture device for puncturing a skin by a puncture needle, the puncture device comprising:

a puncture needle having a needlepoint and a curvature portion curved along the lengthwise direction of the puncture needle;

a retaining member for retaining the puncture needle;

an indwelling device configured to be indwelled in a living body by said puncture needle; and a guide member mounted at a predetermined position of a body surface, wherein said puncture needle is configured to move along said guide member to puncture said skin, and wherein the puncture device is configured to prevent the needlepoint from protruding out of a surface of the skin while the puncture needle punctures the skin.

3. The puncture device according to claim 2, wherein a curved surface of such a shape along the curvature of said puncture needle is formed on said guide member.

4. The puncture device according to claim 3, wherein there is formed on said retaining member a curved surface of such a shape along a curved surface which is formed on said guide member.

5. The puncture device according to claim 1, wherein said puncture needle moves on a turning trajectory having a predetermined turning radius, and the needlepoint of said puncture needle moves at least until the lowest point of said turning trajectory.

6. The puncture device according to claim 2, wherein said puncture needle moves on a turning trajectory having a predetermined turning radius, and the needlepoint of said puncture needle moves at least until the lowest point of said turning trajectory.

7. The puncture device according to claim 2, wherein a dermis layer is positioned on the lower side of said guide member such that said puncture needle is stuck in a state in which a tip portion including the needlepoint of said puncture needle becomes approximately parallel with respect to the body surface.

8. A puncture device for puncturing a skin by a puncture needle, the puncture device comprising:

curved along the lengthwise direction of the puncture needle;

a retaining member for retaining this puncture needle;

an indwelling device configured to be indwelled in a living body by said puncture needle;

a fixing member for fixing said indwelling device; and a guide member mounted at a predetermined position of the body surface, wherein said puncture needle is configured to move along said guide member to puncture said skin.

9. The puncture device according to claim 8, wherein a curved surface of such a shape along the curvature of said puncture needle is formed on said guide member.

10. The puncture device according to claim 9, wherein there is formed on said retaining member a curved surface of such a shape along a curved surface which is formed on said guide member.

11. The puncture device according to claim 8, wherein said puncture needle moves on a turning trajectory having a predetermined turning radius, and a needlepoint of said puncture needle moves at least until the lowest point of said turning trajectory.

12. A puncture method for puncturing a skin by a puncture needle, the puncture method using:

a device main body having a contact surface which contacts said skin;

a puncture needle having a needlepoint and a curvature portion curved along the lengthwise direction of the puncture needle and possessing a predetermined curvature radius; an indwelling device configured to be indwelled in a living body by said puncture needle; and a puncture needle moving means provided in said device main body, the method comprising moving said puncture needle by said puncture needle moving means to move along a circular trajectory which said curvature radius draws so that the puncture needle punctures said skin while the needlepoint is prevented from protruding out of a surface of the skin.

13. A method of puncturing skin comprising:

positioning a puncture device relative to skin such that a contact surface of a device main body of the puncture device contacts skin, the puncture device also comprising a puncture needle having a needlepoint and a curvature portion curved along the lengthwise direction of the puncture needle and possessing a curvature radius the puncture device also comprising an indwelling device configured to be indwelled in a living body by said puncture needle;

moving the puncture needle along a circular trajectory which the curvature radius draws to puncture the skin at a first point with the needlepoint;

moving the puncture needle along the circular trajectory to withdraw the puncture needle from the skin; and wherein, between a time when the needlepoint punctures the skin at the first point and a time when the puncture needle is withdrawn from the skin, the needlepoint does not protrude out of the skin.

* * * * *

UNITED STATES PATENT AND TRADEMARK OFFICE
CERTIFICATE OF CORRECTION

PATENT NO.        : 7,611,492 B2
APPLICATION NO.   : 11/594925
DATED             : November 3, 2009
INVENTOR(S)       : Yutaro Sonoda et al.

It is certified that error appears in the above-identified patent and that said Letters Patent is hereby corrected as shown below:

Col. 15, line 30 in claim 5, change "claim 1" to --claim 4--.

Col. 15, line 47 in claim 8, before "curved" please insert --a hollow puncture needle having a curvature portion--.

Signed and Sealed this

Twenty-first Day of December, 2010

David J. Kappos
*Director of the United States Patent and Trademark Office*